US00PP09857P

United States Patent [19]

Nies

[11] Patent Number: Plant 9,857

[45] Date of Patent: Apr. 15, 1997

[54] CHERRY TREE 'FIRM RED'

[76] Inventor: Marvin L. Nies, 9296 E. Kettleman La., Lodi, Calif. 95240

[21] Appl. No.: 520,209

[22] Filed: Aug. 21, 1995

[51] Int. Cl.[6] ..... A01H 5/00

[52] U.S. Cl. ..... Plt./37

[58] Field of Search ..... Plt./37

*Primary Examiner*—James R. Feyrer

[57] ABSTRACT

Hardy, heat tolerant, vigorous, large upright tree; moderately spreading similar to 'Garnet', the pollen parent. Current mature leaves are large, ovate, acuminate, and acutely pointed, having margins like those of the seed parent 'Large Red'. Blooms 4 days after 'Garnet' and 'Large Red'; has a slightly higher chilling requirement than either; setting well in wet weather with no straggle bloom, for a one-shot harvest. Very large, uncommonly firm fruit has long, medium-thick stems; is exceptionally crack-free, even in wet, rainy weather, setting precedence. Fully matures 5 days after 'Giant Red', 3 days after 'Garnet' and 'Bing' at Lodi. Flesh is firm, crisp, uniform in maturity and size; having stems shorter than 'Large Red' but longer than 'Garnet'. Fruit is evenly distributed along the branches throughout tree. Fruit per bud is 1, but mostly 2 and 3. Annually crops are even and stable. Skin color is shiny red maturing to red-black. Flesh is about 40% firmer than 'Garnet' and 'Bing', the major mid-season industry standards for firmness. Free-stone fruit has good eating qualities, good flavor, excellent sugar-acid ratio, moderate acidity and solid red skin color. Strongly similar topg,2 'Giant Red' form, with large, prominent, strongly rounded shoulders somewhat compressed in the suture plane; large, circular, deep flaring stem cavity unlike 'Garnet', and less rounded on the ventral surface from base to apex, with the ventral surface being somewhat flatter, with similar prominent, strongly rounded shoulders.

1 Drawing Sheet

FIELD OF INVENTION

The present variety of cherry tree has been denominated varietally as 'Firm Red', however, the fruit produced will be marketed under the Trade Mark "Late Garnet". This variety is the outgrowth of a plant breeding program which has been conducted by me on a continuous basis since 1957 in my Experimental Orchard near Lodi, County of San Joaquin, Calif. One part of the program has been to develop new and distinct varieties of cherries to be grown commercially in the warmer, lower humidity, lower chilling earlier production areas, with the tree to have adequate heat tolerance, fruit that is free of sutures, spurs and doubles in hotter climates, holding on the tree well without ripening too quickly, fruit that is very large, with very firm flesh, skin that is adequately thick, short thick stems, high soluble solids, moderate acidity, pleasing sugar/acid ratio, non astringent, non-browning skin and flesh and with adequate disease and insect resistance. The present variety has achieved these objectives with the exception that the skin has a slight suggestion of tannin and a small percentage of sutures in the hotter climates. All of the above qualities, with the exceptions noted, make this selection an excellent candidate for the ultimate commercialization of the variety. The present cherry tree is embraced by Subclass 37, Plants, of the Plant Patent Office, MANUAL OF CLASSIFICATION.

PRIOR VARIETIES

Among the existing varieties of cherry trees which are known to me are those mentioned herein; to-wit *Prunus mahaleb* rootstock (unpatented), 'Colt' rootstock (U.S. Plant Pat. No. 4,059), 'Ruby' (U.S. Plant Pat. No. 4,436), 'Garnet' (U.S. Plant Pat. No. 4,431), 'Bing' (unpatented), 'Large Red' (U.S. Plant patent application Ser. No. 08/512,696), 'Early Red' (U.S. Plant Pat. No. 9,368) and 'Giant Red' (U.S. Plant patent application Ser. No. 08/515,923).

ORIGIN OF THE VARIETY

The present variety, denominated varietally as 'Firm Red' relates to a distinct variety of cherry tree originated by me, the fruit of which was first observed by me in 1982 in the seedling block of my experimental orchard in a cultivated area at the Marvin L Nies Ranch near Lodi, County of San Joaquin, Calif., and was initiated in 1976 by crossing the selected seed parent 'Large Red' with the selected pollen parent 'Garnet', which resulted in seeds from the seed parent, which when germinated and grown, produced some seedlings, one of which was the present variety; the location of which in the seedling block was recorded in my Breeding Records as Seedling T 6-324-6, and which when grown to maturity, evidenced novel and distinctive characteristics, and I therefore selected it for asexual reproductions preparatory to patenting and ultimate commercial growing thereof.

ASEXUAL REPRODUCTION OF THE VARIETY

Subsequent to the origination of the present variety of cherry tree I asexually reproduced the selection on *Prunus mahaleb* rootstock and at a later date on Colt rootstock in my experimental orchard near Lodi, County of San Joaquin, Calif., by budding and grafting, and such reproduction of plant and fruit characteristics were true to the original plant at maturity in all respects.

SUMMARY OF VARIETY

My first observation of the fruit of this variety was made in 1982 in my experimental orchard seedling block in Lodi, San Joaquin County, Calif. and what set the present variety apart from the sister seedlings was the shiny dark red color, very large sized fruit, fruit that was even in maturity when picking ripe, and that was exceptionally firm, hard and crisp; and on further observation in subsequent years of the seedling tree and grafted trees, the following traits were observed; the present variety was very vigorous, spreading tree with good form, being similar to 'Garnet'; leaves that were large on current years mature growth, ovate, acuminate, acutely pointed, margins of the blades coarsely crenate; with the whorl of leaves emanating from spurs of second years growth smaller and variable in size, generally five (5)

per spur-one (1) or two (2) very small leaves with the rest somewhat larger and of different sizes; with margins on these small leaves finely crenate, sometimes serrate towards the petiole; blooming fourteen (14) days after 'Early Red' (patent pending. 'Early Garnet' ™), eight (8) days after 'Ruby', five (5) days after 'Giant Red', four (4) days after 'Garnet' and two (2) days after 'Large Red'; the flesh of the fruit being very hard and crisp, estimated to be forty percent (40%) firmer than 'Bing' and 'Garnet' (the industry standards for firmness); a stone that was free, separating smoothly from the flesh on reaching full maturity, developing significally darker red, softer flesh on the basal portion of the cavity when red ripe; fairly long fruit stems that were generally not as long as those of 'Large Red', equal to those of 'Giant Red', longer than those of 'Ruby', much longer than those of 'Garnet' and very much longer than those of 'Early Red'; the fruit having red flesh and juice when the skin was red in color, very very dark red flesh and juice when the skin darkened towards a reddish black color. In the knowledge of the originator, this variety is precedent setting, in that it is the first very very firm, hard, crisp cherry that is also highly crack resistant, with less than five (5%) cracks during the historic wet harvest season of 1995; it being commonly acknowledged by horticulturalists that up to the present time only very soft fleshed cherry varieties, that have not been acceptable in the commercial marketplace, have exhibited significant crack resistance. The present variety is a departure from this traditional observation. All of the present firm commercial varieties presently grown are subject to severe cracking in most instances in wet weather, and during the historic 1995 wet harvesting season, 'Bing', the major commercial variety presently grown, sustained from forty percent (40%), in many cases, up to almost one hundred percent (100%) cracks, as compared to 'Large Red' and 'Ruby' which developed approximately forty percent (40%) cracks, the present variety developing less than five percent (5%) cracks, with no moon cracks. At the present time, with the current commercial varieties, there is not only a substantial loss in the value of the fruit that is not marketed but also the cost of picking and subsequent handling of the cull fruit during the packing operation. The above facts clearly indicate that in rainy wet years, with trees that are grown in the open, the difference between profit and loss most likely will be dependent on production derived from crack resistant varieties; the present variety generally being picking ripe fourteen (14) days after 'Early Red', nine (9) days after 'Ruby', five (4) days after 'Giant Ruby', three (3) days after 'Garnet', the same time as 'Large Red', and three (3) days before 'Bing'. In summary, the major desirable traits of the present variety are the very very large, shiny, dark red fruit that is uniform in size and maturity, good fruit flavor, high soluble solids, moderate acidity, no spurs and doubles and exceedingly firm, hard, crisp fruit that is highly crack resistant in wet weather. The above qualities all contribute to make the present variety desirable, not only from a production standpoint, but also in the marketplace.

DRAWING

The accompanying photograph exhibits clusters of whole fruits positioned to display the form of the fruit, skin color, stem length on a representative branch with buds, spurs and leaves, with two (2) detached fruits that were sectioned—one (1) cut longitudinally showing the ventral half, with the dorsal side of the stone showing, the dorsal one-half (½) of the fruit showing the smooth stone cavity and the darkened softer flesh on the dorsal edge adjacent to the cavity, a transverse section showing the apical one-half (½), illustrating the color and texture of the flesh and with the basal one-half (½) of the stone showing.

POMOLOGICAL CHARACTERISTICS

The botanical details of this new and distinct variety of cherry tree with color definitions (except those in common color terms) referenced to *The Wilson Colour Chart I and II*, published by The British Colour Council-Horticultural Color Chart (1938) are as follows:

Tree:

*Size.*—Large on *Prunus mahaleb* and Colt rootstocks.
*Vigor.*—Very vigorous.
*Growth.*—Fairly open. Spreading moderately.
*Density.*—Fairly open.
*Form.*—Bushy.
*Hardiness.*—Hardy.
*Production.*—Crops well in inclement weather. Commercially acceptable crop levels from year to year.

Trunk:

*Size.*—Medium.
*Texture.*—Medium.

Branches:

*Size.*—Medium.
*Texture.*—Medium.
*Color.*—Dark brown on younger wood-dull grayish brown on older wood.
*Lenticels.*—Numerous. Very large. Light brown.

Leaves:

*Size.*—First years mature growth — large-average length (25 leaves) 14.8 cm — average width (25 leaves) 6.5 cm. Ratio: width/length 0.44. Leaves emanating from spurs on second years growth — variable in size — very small to medium.
*Veination.*—Large vein centrally oriented from base of blade to apex. Lateral veins oblique towards apex of blade-extending from main central vein forming a looped configuration near margin. No pigmentation.
*Form.*—Ovate. Acuminate. Acutely pointed.
*Thickness.*—Medium.
*Color.*—Top of leaf — Spanish green (0/960). Bottom of leaf — Spanish green (0/960/2). Showing little tendency of margins of leaves to roll upward on older wood.
*Texture.*—Smooth.
*Margins.*—Crenate.
*Petiole.*—Thick. Groove on upper side. On current years mature shoots — quite long-four (4) cm to five (5) cm. Light red on upper surface — Currant red (821/3). Small leaves on spurs of second years wood — no pigmentation. Ratio — petiolelength/length of blade — 0.24 (Average 25 leaves).
*Glands.*—Reniform. Compressed. Glabrous. Located on petiole near blade — some attached to blade. Color — very light red tinge on upper surface in the compressed middle portion of the gland. Located generally adjacent to blade. Number: On the petioles of one year vigorous upright shoots on large leaves — predominately two (2) — very occasionally up to four (4) — offset opposite — the size being quite large. On smaller leaves — much smaller — one (1)— occasionally none — sometimes with an inconspicuous gland on the blade near petiole. On two (2) year shoots that have very small leaf blades — generally eglandular. Sometimes on the somewhat larger blades — occasionally one (1).

*Stipules.*—Two (2) — one (1) on each side of petiole on young leaves.

Flower buds:

*Hardiness.*—Hardy.

*Size.*—Medium.

*Length.*—Medium.

*Form.*—Conic — plump.

Flowers:

*Date of bloom.*—Mar. 12, 1995.

*Petals.*—Number: Five (5). Size — medium large — length 15.0 mm. Width — 12.0 mm. Color — pure white. Striated — shell like appearance. At midpoint — petals touch or are slightly separated from midpoint of the petal to cup the petal narrows obliquely to form a fairly wide separation at the attachment point. One prominent notch on the apex — on some two (2) — occasionally additional smaller notches.

*Filament length.*—5.0 mm to 13.0 mm.

*No. of filaments.*—Almost always twenty five (25) to twenty eight (28).

*Stigma length.*—14.0 mm.

*Hypanthium.*—Medium. Five (5) sepals — no red pigmentation. Strongly reflexed on mature flowers. Very slight reddish tinge on cup.

*Blooming period.*—Compact — no straggle bloom.

*No. of flowers per bud.*—Quite consistently three (3) to four (4).

*Flower stalk.*—Length 3.9 cm. Color — Veronese green (660/2).

Fruit:

*Maturity when described.*—Eating ripe — May 19 1995.

*Date of first picking.*—May 19, 1995. All fruit picked at one time.

*Size.*—Very uniform. Large. Average width — longitudinal plane — 30 mm. Suture plane — 23.6 mm. Maximum width observed — 34 mm. Average size 75/64" (9Row) — 29.8 mm.

*Form.*—Globose. Uniform. Symmetrical in transverse and longitudinal planes — Asymmetrical in suture plane. Very large, prominent shoulders at base. Rounded on ventral surface — strongly rounded on dorsal surface. Longitudinal plane — Sides from mid-point towards apex — rounded — oblique. Some fruit has a strong cleavage on the suture line from base to near midpoint — many times extending to apex — slightly depressed at pistil point.

*Suture.*—Some. Small percentage of the fruit in hotter climates.

*Spurs and doubles.*—None.

*Ventral surface.*—Slightly Rounded from base to apex. Slightly compressed.

*Dorsal surface.*—Strongly rounded. Wide — shallow — very slightly compressed groove midpoint — from base to apex.

*Stem cavity.*—Very prominent — strongly rounded. Circular. Flaring obliquely upward from stem attachment to the midpoint of the shoulders creating a cavity that is 4 mm deep when measured in the longitudinal plane. Shoulders somewhat compressed in the suture plane. The size of the above referenced fruit — width 32.4 mm — longitudinal plane — length 27.0 mm.

*Color.*—Dark red when fully mature with uniform color over the total surface — Currant Red (821/2) — progressing to a reddish black on further maturity.

*Base.*—Shoulders very prominent — very strongly rounded. Stem cavity wide — large — deep — very pronounced.

*Apex.*—Rounded.

*Pistil point.*—Apical. An inconspicuous brown abscission point.

*Ripening span.*—Very even ripening. One picking.

Skin:

*Thickness.*—Medium.

*Texture.*—Medium.

*Tenacity.*—Tenacious to flesh.

*Tendency to crack.*—None in dry weather. Precedent setting crack resistance for a very very firm fruit.

*Color.*—Mature fruit — picking ripe — Currant Red — (8/21).

*Down.*—Wanting.

*Surface.*—Shiny — glassy appearance.

Flesh:

*Color.*—Fully mature fruit — Red — Currant Red (821/2).

*Surface of pit cavity.*—Red — Currant Red (8/21).

*Amygdalin.*—Wanting.

*Texture.*—Firm — fine — meaty.

*Aroma.*—Wanting.

*Fibres.*—Few — very fine.

*Ripens.*—Very evenly.

*Flavor.*—Good at full maturity.

*Eating quality.*—Good. High soluble solids. Low to moderate acidity. Excellent sugar/acid ratio.

*Tendency to crack.*—None in dry weather. Two percent (2%) to five percent (5%) in very wet weather.

Stone:

*Type.*—Free.

*Size.*—Medium large. Average length — 11.0 mm. Average width — 7.0 mm. Average breadth 9.0 mm.

*Form.*—Globose.

*Base.*—Slightly oblique.

*Hilum.*—Long. Narrow. Oblong.

*Apex.*—Pointed.

*Sides.*—Equal. Symmetrical.

*Surface.*—Smooth. Ridges forming wide, shallow, furrows one third (⅓) of the distance from hilum towards apex.

*Ridges.*—Jagged.

*Ventral edge.*—Flattened. Elliptical. Width — four (4) mm at midpoint of stone. Edge rounded from base to apex, Three (3) prominent ridges from hilum to apex — one very prominent — sharp central winged ridge that extends away from the main contour of the stone near the base two (2) mm. Two (2) smaller sharp lateral ridges form a narrow — pointed elliptical configuration with the point near apex — extending at midpoint away from the central ridge two (2) mm on each side.

*Dorsal edge.*—Sharp ridge — starting slightly below hilum to apex.

*Color.*—Egyptian Buff (407/1).

*Form.*—Oval. Flattened on ventral side. Strongly rounded on dorsal side from hilum to apex.

*Taste.*—Seed very bitter.

*Viability.*—Low.

*Amygdalin.*—Abundant.

Use: Market. Dessert. Shipping.

Keeping quality: Exceptional.

Resistance to insects and diseases: No unusual susceptibilities noted.

Shipping quality: Excellent — both local and long distance.

Variance in botanical details: Although the new variety of cherry possesses the described characteristics under the ecological conditions at Lodi, Calif., in the Northern part of the San Joaquin Valley, it is to be expected some variations in some of these pomological characteristics may occur when grown in areas with different climatic conditions, different soil types.

I claim:

1. A new and distinct variety of cherry tree, substantially as illustrated and described: a very vigorous, large tree with a tree habit semi-upright and semi-open, hardy and heat tolerant; leaves large, ovate, acuminate, acutely pointed, with leaf margins coarsely crenate, setting from one (1) to three (3) fruits per fruit bud, the fruit being very very large and uniform in size with even distribution of fruit the length of the branches and throughout the tree, blooming four (4) days later than 'Garnet' and 'Large Red', indicating a slightly higher chilling requirement than either parent; a moderately heavy bloom, with large flowers that have an open appearance; flower cup with a slight reddish tinge with no pigment on the sepals; fairly long, medium thick unpigmented fruit stems that are not as long as the stems of 'Large Red', the seed parent, but considerably longer than Garnet the pollen parent; fruit firm hard and crisp, shiny red skin color when picking ripe, with a red to reddish black pigmented line from base to apex on the suture line, skin of the fruit turning dark red at full maturity with very very dark red flesh and juice; the fruit being very similar in form to 'Giant Red', with very prominent rounded shoulders that accentuate a circular, deep, flaring stem cavity, being strongly rounded on the dorsal side with a very shallow almost inconspicuous compressed groove from base to apex, moderately rounded on the ventral side; a fairly long medium thick stem that is shorter than that of 'Large Red', the seed parent, but much longer than that of 'Garnet', the pollen parent; the size of the fruit being somewhat larger than the large fruited 'Garnet' and 'Large Red' varieties, and equal in size to the very very large size of 'Giant Red'; being considerably firmer and harder than 'Garnet', 'Large Red' and 'Giant Red', with more firmness than any other commercial variety known to the originator; picking ripe five (5) days after 'Giant Red', three (3) days after 'Garnet', the same timing as 'Large Red'; the present variety being the only exceedingly firm, hard, crisp fruit, known to the originator, that is almost crack free in extremely wet weather conditions during harvest; with few sutures but no spurs or doubles in the hotter Central Valley of Northern California.

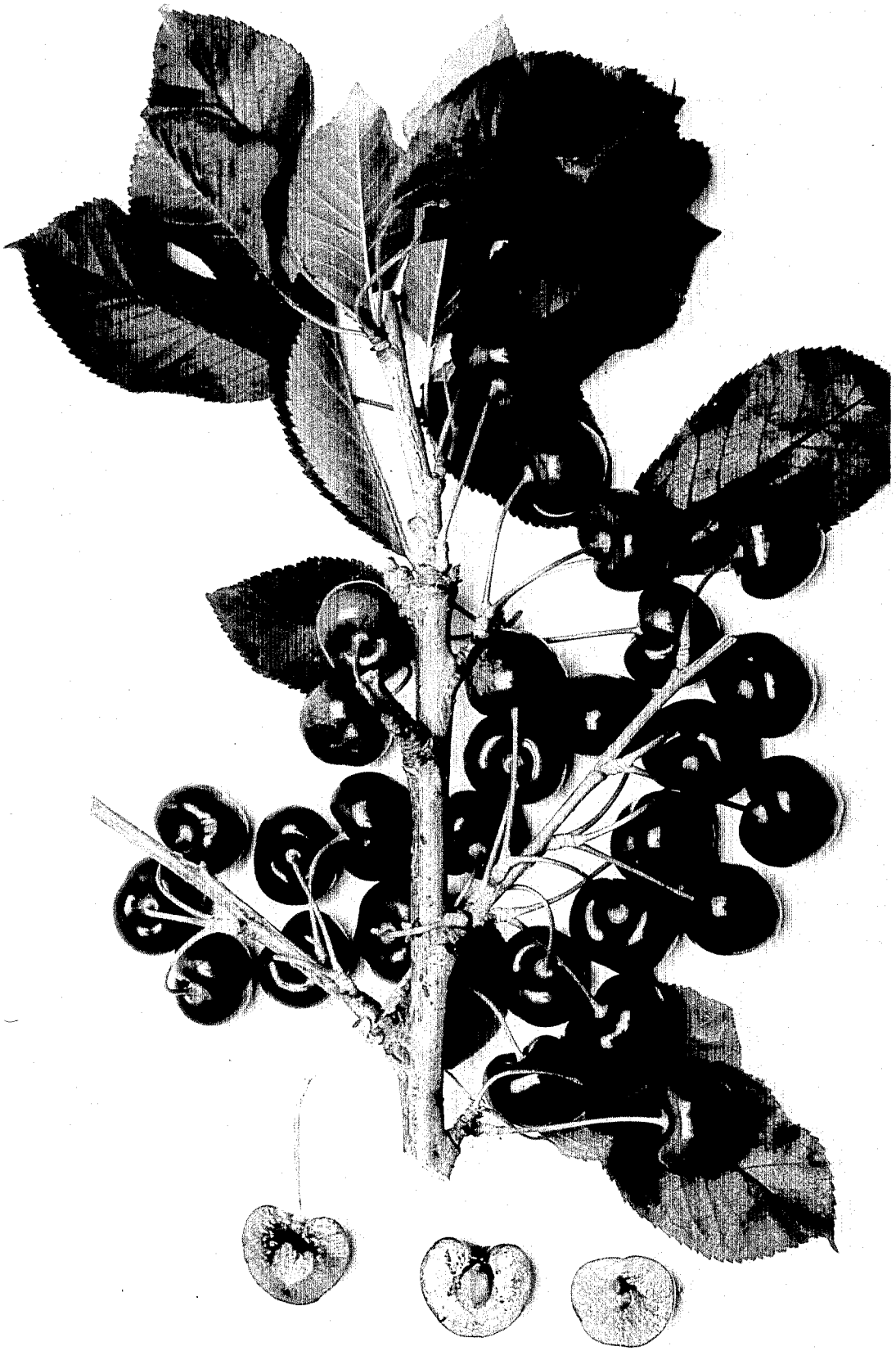

* * * * *